United States Patent
Carley et al.

(10) Patent No.: US 7,001,398 B2
(45) Date of Patent: Feb. 21, 2006

(54) CLOSURE DEVICE AND METHODS FOR MAKING AND USING THEM

(75) Inventors: Michael T. Carley, San Jose, CA (US); Richard S. Ginn, San Jose, CA (US); Javier Sagastegui, Castro Valley, CA (US); Ronald J. Jabba, Redwood City, CA (US); William N. Aldrich, Napa, CA (US); W. Martin Belef, San Jose, CA (US)

(73) Assignee: Integrated Vascular Systems, Inc., Sunnyvale, CA (US)

( * ) Notice: Subject to any disclaimer, the term of this patent is extended or adjusted under 35 U.S.C. 154(b) by 194 days.

(21) Appl. No.: 10/617,090

(22) Filed: Jul. 9, 2003

(65) Prior Publication Data

US 2004/0010285 A1 Jan. 15, 2004

Related U.S. Application Data

(60) Division of application No. 10/081,726, filed on Feb. 21, 2002, now Pat. No. 6,623,510, which is a continuation-in-part of application No. 09/732,178, filed on Dec. 7, 2000, now Pat. No. 6,719,777.

(51) Int. Cl.
*A61B 17/10* (2006.01)

(52) U.S. Cl. .................... 606/142; 606/139; 606/216; 606/221

(58) Field of Classification Search .............. 606/139, 606/142, 143, 151, 157, 213, 215–216, 219–221
See application file for complete search history.

(56) References Cited

U.S. PATENT DOCUMENTS 5,674,231 A * 10/1997 Green et al. ............... 606/142

(Continued)

FOREIGN PATENT DOCUMENTS

WO    WO 00/56223    9/2000

(Continued)

OTHER PUBLICATIONS

Derowe, A. et al., "Vascular Port Device" PCT Publication No. WO 99/62408, Dec. 9, 1999.

*Primary Examiner*—Eduardo C. Robert
*Assistant Examiner*—D. Jacob Davis
(74) *Attorney, Agent, or Firm*—Workman Nydegger

(57) ABSTRACT

A method for closing an opening in a wall of a body lumen wherein an elongate member is advanced into the body lumen and a distal portion of an obturator is positioned distally beyond the distal end of the elongate member within the body lumen and in which one or more expandable elements on the distal portion of the obturator are expanded. The obturator is then withdrawn until the expandable elements contact the wall of the body lumen and a clip having tines is advanced over the elongate member until the tines penetrate the wall of the body lumen. The tines and the expandable elements are offset from one another. The elongate member is withdrawn from the body lumen and the clip substantially closes the opening in the body lumen.

9 Claims, 8 Drawing Sheets

U.S. PATENT DOCUMENTS

| | | |
|---|---|---|
| 6,113,612 A | 9/2000 | Swanson et al. |
| 6,152,937 A | 11/2000 | Peterson et al. |
| 6,582,452 B1 | 6/2003 | Coleman et al. ............ 606/213 |
| 6,602,263 B1 * | 8/2003 | Swanson et al. ............ 606/153 |
| 6,623,510 B1 | 9/2003 | Carley et al. |
| 6,726,704 B1 | 4/2004 | Loshakove et al. |
| 6,926,731 B1 | 8/2005 | Coleman et al. ............ 606/213 |

FOREIGN PATENT DOCUMENTS

| | | |
|---|---|---|
| WO | WO 00/56227 | 9/2000 |

* cited by examiner

CLOSURE DEVICE AND METHODS FOR MAKING AND USING THEM

CROSS-REFERENCE TO RELATED APPLICATIONS

This application is a division of application Ser. No. 10/081,726, filed Feb. 21, 2002, now U.S. Pat. No. 6,623,510, which application is a continuation-in-part of application Ser. No. 09/732,178, filed Dec. 7, 2000, now U.S. Pat. No. 6,719,777 for "Closure Device and Methods for Making and Using Them," the disclosures of which are expressly incorporated by reference herein.

FIELD OF THE INVENTION

The present invention relates generally to apparatus and methods for engaging tissue and/or closing openings through tissue, and more particularly to devices for closing a puncture in a blood vessel or other body lumen formed during a diagnostic or therapeutic procedure, and to methods for making and using such devices.

BACKGROUND

Catheterization and interventional procedures, such as angioplasty or stenting, generally are performed by inserting a hollow needle through a patient's skin and intervening tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

U.S. Pat. No. 5,478,354, issued to Tovey et al., discloses a surgical fastener including an annular base having legs that, in a relaxed state, extend in a direction substantially perpendicular to a plane defined by the base and slightly inwards toward one another. During use, the fastener is fit around the outside of a cannula, thereby deflecting the legs outward. The cannula is placed in an incision, and the fastener is slid along the cannula until the legs pierce into skin tissue. When the cannula is withdrawn, the legs move towards one another back to the relaxed state to close the incision.

U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. Sides of the ring may be squeezed to separate the barbs further, and the barbs may be engaged into tissue on either side of a wound. The sides may then be released, causing the barbs to return closer together, and thereby pulling the tissue closed over the wound. These staples, however, have a large cross-sectional profile and therefore may not be easy to deliver through a percutaneous site to close an opening in a vessel wall.

Accordingly, devices for engaging tissue, e.g., to close a vascular puncture site, would be considered useful.

SUMMARY OF THE INVENTION

The present invention is directed to devices and methods for engaging tissue, e.g., to connect tissue segments together or to close and/or seal openings through tissue, such as in a wall of a body lumen. More particularly, the present invention is directed to vascular closure devices or clips for closing a puncture in a wall of a blood vessel formed during a diagnostic or therapeutic procedure, and to methods for making and using such devices.

In one aspect of the present invention, a device for engaging tissue includes a generally annular-shaped body defining a plane and disposed about a central axis extending substantially normal to the plane. The body may be movable from a substantially planar configuration lying generally in the plane towards a transverse configuration extending out of the plane. The body may also include a plurality of looped elements including alternating first and second curved regions that define an inner and outer periphery of the body, respectively, in the planar configuration. A plurality of tines or other tissue-engaging elements may extend from the first curved regions, and may be oriented towards the central axis in the planar configuration, and substantially parallel to the central axis in the transverse configuration. The device may be biased towards the planar configuration, e.g., to bias the tines towards the central axis.

The looped elements of the device may generally define an endless zigzag pattern, e.g., a sinusoidal pattern, extending about the central axis. The looped elements may facilitating deforming the device between the planar and transverse configurations, e.g., by distributing stresses through the device and minimizing localized stresses in the curved regions. In addition, the looped elements may be expandable between expanded and compressed states for increasing and reducing a periphery of the body in the transverse orientation, respectively. The looped elements may be biased towards one of the compressed and expanded states.

Adjacent tines of the device may have a first curved region disposed between them. The first curved region between adjacent tines may include a substantially blunt element extending towards the central axis. The blunt element may have a length shorter than lengths of the adjacent tines.

In addition or alternatively, the tines of the device may include first and second primary tines, having a first length and a second length, respectively, which may be the same as or different than one another. The first and second primary tines may be disposed on opposing first curved regions, and may be oriented substantially towards each other in the planar configuration. In the planar configuration, the first and second primary tines may at least partially overlap. The tines may also include one or more secondary tines having a length substantially shorter than the first and second lengths of the primary tines. The secondary tines may be disposed on either side of the first and second primary tines.

In another aspect of the present invention, a device for engaging tissue includes a generally annular-shaped body defining a plane and disposed about a central axis extending substantially normal to the plane. The body may be movable from a substantially planar configuration lying generally in the plane towards a transverse configuration extending out of the plane. A first primary tine, having a first length, may extend from the body towards the central axis in the planar configuration, and may be deflectable out of the plane when the body is moved towards the transverse configuration. A second primary tine, having a second length, may extend from the body towards the first tine when the body is in the planar configuration, and may be deflectable out of the plane when the body is moved towards the transverse configuration. The lengths of the first and second primary tines may cause the primary tines to at least partially overlap in the planar configuration. The body may be biased towards the planar configuration to bias the tines generally towards the central axis.

The device may include a set of secondary tines having a length shorter than the first and second lengths. The secondary tines may extend from the body towards the central axis in the planar configuration, and may be deflectable out of the plane when the body is moved towards the transverse configuration. In an exemplary embodiment, a secondary tine may be disposed on either side of the first primary tine, and a secondary tine may be disposed on either side of the second primary tine.

Optionally, adjacent tines may have a first curved region disposed between them. The first curved region between adjacent tines may include a substantially blunt element extending towards the central axis. The blunt element may have a length shorter than lengths of the adjacent tines.

Also, the device may include a plurality of looped elements disposed around a periphery of the body. The looped elements may generally define an endless zigzag pattern extending about the central axis. The first primary tine and the second primary tine may extend from looped elements disposed opposite one another. The looped elements may be expandable between expanded and compressed states for increasing and reducing a periphery of the body in the transverse orientation, respectively. The looped elements may be biased towards one of the compressed and expanded states.

In another aspect of the present invention, a method is provided for manufacturing a clip from an elastic material, such as a sheet of superelastic alloy, e.g., a nickel-titanium alloy ("Nitinol"). The components of the clip, e.g., a generally-annular body, optionally including looped elements, and/or tines, may be formed by removing portions from the sheet. The portions may be removed, e.g., by laser cutting, chemical etching, photo chemical etching, stamping, electrical discharge machining, and the like. The clip may be polished using one or more processes, such as electropolishing, chemical etching, tumbling, sandblasting, sanding, and the like, and/or heat-treated to provide a desired finish and/or desired mechanical properties. Optionally, the body and tines may be coated with a therapeutic agent, e.g., a peptide coating and/or one or more clotting factors.

In addition or alternatively, the clip may be disposed in a planar configuration, e.g., upon forming the clip from the sheet, and heat treated to form a clip biased to the planar configuration. For example, the clip may be formed from a shape memory material, e.g., Nitinol, that may substantially recover the planar configuration when heated to a first predetermined temperature corresponding to an austenitic state, e.g., a temperature close to body temperature. The clip may be cooled to a second predetermined temperature corresponding to a martensitic state, e.g., a temperature at or below ambient temperature, and malleably manipulated.

For example, the clip formed from the sheet may be deformed to a transverse configuration, such as that described above, e.g., by loading the clip onto a mandrel or directly onto a delivery device. If the clip includes looped elements formed from the body, the looped elements may be biased upon heat treatment towards an expanded state, but may be malleably deformed to a compressed state upon cooling, e.g., to facilitate loading onto the delivery device. Alternatively, the clip may be formed from a superelastic material, e.g., Nitinol, such that the clip may be resiliently deformed to the transverse configuration and/or compressed state, yet may automatically attempt to resume its planar configuration and/or expanded state upon release from external forces.

In still another aspect of the present invention, a method for closing an opening in a wall of a body lumen is provided. The distal end of an elongate member may be advanced through an opening in a patient's skin, along a passage through tissue, and into the body lumen. A distal portion of an obturator may be positioned distally beyond the distal end of the elongate member along the passage within the body lumen. One or more expandable elements on the distal portion of the obturator may be expanded transversely. The obturator may be withdrawn from the passage until the expandable elements contact the wall of the body lumen, thereby providing a tactile indication of a location of the wall of the body lumen between the elongate member and the plurality of expandable elements of the obturator.

A clip may be advanced into the passage over the elongate member until tines of the clip penetrate the wall of the body lumen, the tines and the expandable elements on the obturator being angularly offset from one another such that the tines penetrate the wall at locations between the expandable elements. The obturator may be collapsed, and the elongate member and/or obturator may be withdrawn from the body lumen and passage, leaving the clip to substantially close the opening in the wall of the body lumen. When the elongate member is withdrawn, the tines may automatically at least partially move towards a planar configuration to substantially close the opening.

The tines of the clip may include primary tines and secondary tines. Here, advancing the clip may include puncturing the wall of the body lumen with the primary tines until tips of the primary tines enter the body lumen, and puncturing the wall of the body lumen with the secondary tines. The primary tines and the secondary tines may puncture the walls without contacting the expandable elements of the obturator.

Other objects and features of the present invention will become apparent from consideration of the following description taken in conjunction with the accompanying drawings.

DETAILED DESCRIPTION OF THE PREFERRED EMBODIMENTS

Figure 1A:
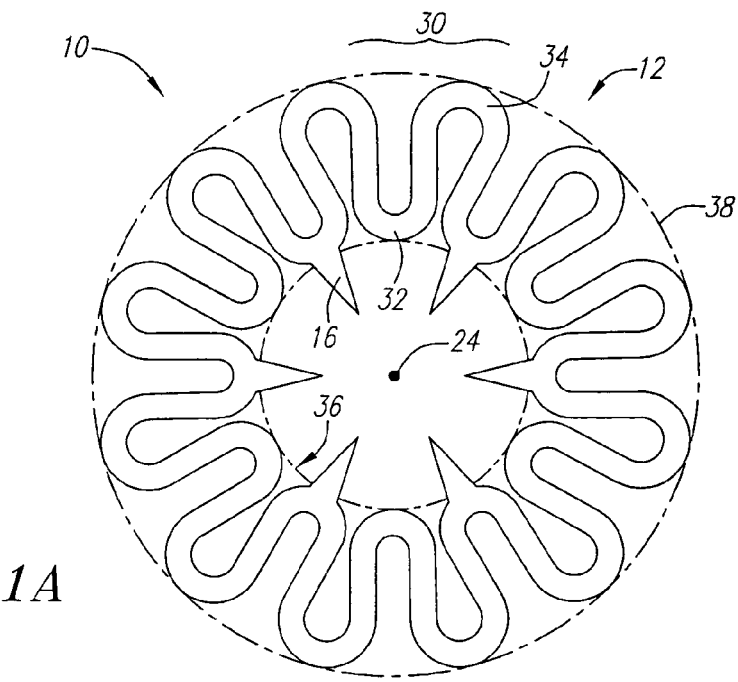
FIG. 1A is a top view of a first embodiment of a clip including a plurality of tines in a planar orientation, in accordance with the present invention.
Figure 1B:
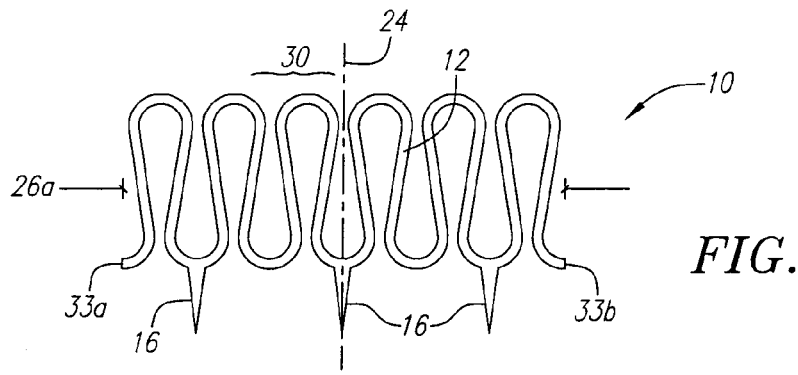
FIGS. 1B and 1C are side views of the clip of FIG. 1A, with the tines oriented substantially transversely from the planar orientation, in compressed and expanded states, respectively.
Figure 1C:
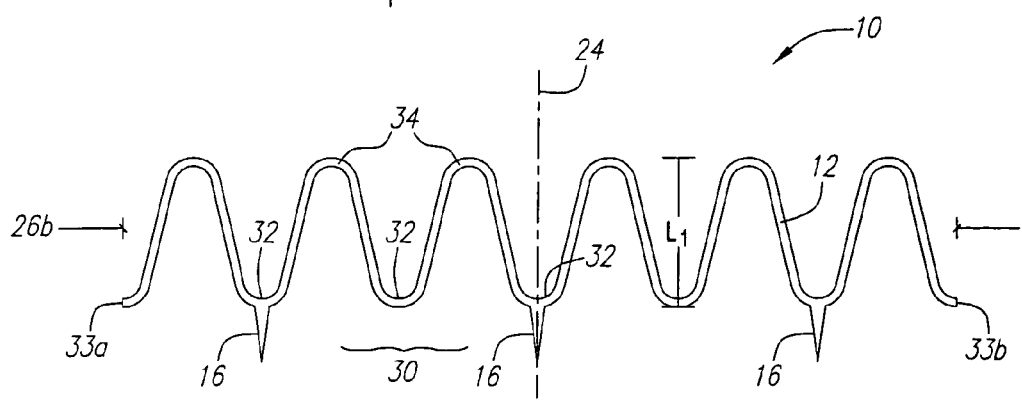

Turning now to the drawings, FIGS. 1A–1C show a first preferred embodiment of a closure device or clip 10 for closing an incision, puncture, or other passage through tissue, e.g., communicating with a blood vessel or other body lumen (not shown). The clip 10 includes a body 12, which may be generally annular in shape and surrounds a central axis 24, and a plurality of tines 16 extending from the body 12. As used herein, an "annular-shaped body" includes any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis.

The body 12 may include a plurality of looped or curved elements 30 that are connected to one another to form the body 12. Each looped element 30 may include an inner or first curved region 32 and an outer or second curved region 34. In a preferred embodiment, the first and second curved regions 32, 34 are out of phase with one another and are connected alternately to one another, thereby defining an endless sinusoidal pattern. Alternatively, other generally zigzag patterns may be provided that repeat periodically, e.g., saw tooth or square tooth patterns (not shown), instead of a sinusoidal pattern, thereby defining inner and outer regions that alternate about the body 12. When the clip 10 is in a substantially planar configuration, as shown in FIG. 1A, the first curved regions 32 may define an inner periphery 36 of the body 12 and the clip 10, and the second curved regions 34 may define an outer periphery 38.

The plurality of tines 16 may be biased to extend generally inwardly, e.g., towards one another and/or towards the central axis 24. The tines 16 may be disposed on the first curved regions 32, and oriented toward the central axis 24 when the clip 10 is in the planar configuration. In a preferred embodiment, the tines 16 may be provided in pairs opposite from one another or provided otherwise symmetrically with respect to the central axis 24.

The tines 16 may include a variety of pointed tips, such as a bayonet tip, and/or may include barbs (not shown) for penetrating or otherwise engaging tissue. For example, to increase the penetration ability of the clip 10 and/or to lower the insertion force required to penetrate tissue, each tine 16 may include a tapered edge (not shown) extending towards the tip along one side of the tine 16. Alternatively, each tine 16 may be provided with a tapered edge on each side of the tine 16 extending towards the tip.

Additionally, as shown in FIGS. 1A–1C, the tines 16 may be disposed on alternating first curved regions 32. Thus, at least one period of a zigzag pattern may be disposed between adjacent tines 16, which may enhance flexibility of the clip 10, as explained further below.

As shown in FIGS. 1B and 1C (where opposite ends 33a, 33b are connected to one another), the body 12 and/or the tines 16 may be deflected such that the tines 16 extend transversely with respect to the plane defined in the planar configuration, thereby defining a transverse configuration for the clip 10. Preferably, the tines 16 are oriented substantially parallel to the central axis 24 in the transverse configuration, as shown in FIG. 1B. In the transverse configuration, the body 12 may have a generally annular shape defining a length, $L_1$, that extends generally parallel to the central axis 24, and corresponds generally to an amplitude of the zigzag pattern. Preferably, the body 12 is sufficiently flexible such that the clip 10 may assume a generally circular or elliptical shape (not shown), e.g., conforming to an exterior surface of a delivery device (not shown) used to deliver the clip 10.

In a preferred embodiment, the tines 16 and/or body 12 are biased to move from the transverse configuration towards the planar configuration of FIG. 1A. Thus, with the tines 16 in the transverse configuration, the tines 16 may penetrate and/or be engaged with tissue at a puncture site. When the clip 10 is released, the tines 16 may attempt to return towards one another as the clip 10 moves towards the planar configuration, thereby drawing the engaged tissue together and substantially closing and/or sealing the puncture site, as explained further below.

The looped elements 30 may distribute stresses in the clip 10 as it is deformed between the planar and transverse configurations, thereby minimizing localized stresses that may otherwise plastically deform, break, or otherwise damage the clip 10 during delivery. In addition, when the clip 10 is in the transverse configuration, the looped elements 30 may be movable between a compressed state, such as that shown in FIG. 1B, and an expanded state, such as that shown in FIG. 1C. Preferably, the looped elements 30 are biased towards the expanded state, but may be compressed to the compressed state, e.g., by constraining the clip 10. Alternatively, only a portion of the looped elements 30 may be biased towards the expanded state, e.g., the first curved regions 32, and/or the looped elements 30 may be biased towards the compressed state. Furthermore, the looped elements 30 reduce the force required to be exerted on the clip 10 to transition the clip 10 from the planar configuration to the transverse configuration before loading onto a delivery device (not shown).

With the clip 10 in the transverse configuration, the looped elements 30 may be circumferentially and/or radially compressed to the compressed state until the clip 10 defines a first diameter or circumference 26a, such as that shown in FIG. 1B. The clip 10 may be constrained in the compressed state, e.g., by loading the clip 10 onto a carrier assembly of a delivery device (not shown), as described further below. When released from the constraint, e.g., when deployed from the carrier assembly, the clip 10 may automatically expand towards the expanded state, such as that shown in FIG. 1C, thereby defining a second diameter or circumference 26b. Thus, the looped elements 30 may facilitate reducing the profile of the clip 10 during delivery, e.g., to facilitate introducing the clip 10 through a smaller puncture or passage. Once the clip 10 is deployed entirely from the delivery device, the looped elements 30 may resiliently expand as the clip 10 returns towards the planar configuration, as explained further below.

To manufacture the clip 10 (or, similarly, any of the other clips described herein), the body 12 and the tines 16 may be integrally formed from a single sheet of material, e.g., a superelastic alloy, such as a nickel-titanium alloy ("Nitinol"). Portions of the sheet may be removed using conventional methods, such as laser cutting, chemical etching, photo chemical etching, stamping, using an electrical discharge machine (EDM), and the like, to form the clip. The tines 16 may be sharpened to a point, i.e., tips may be formed on the tines 16 using conventional methods, such as chemical etching, mechanical grinding, and the like.

The clip 10 may be polished to a desired finish using conventional methods, such as electro-polishing, chemical etching, tumbling, sandblasting, sanding, and the like. Polishing may perform various functions depending on the method used to form the clip 10. For a clip formed by laser cutting or using an EDM, polishing may remove heat affected zones (HAZ) and/or burrs from the clip. For a clip formed by photo chemical etching, polishing may create a smoother surface finish. For a clip formed by stamping, polishing may remove or reduce burrs from the bottom side of the clip, and/or may smooth the "roll" that may result on the topside of the clip from the stamping process.

In addition or alternatively, the clip 10 may be formed from a shape memory alloy, e.g., Nitinol, with the looped elements 30 formed initially in the compressed state and/or the clip 10 in the planar configuration. With the clip 10 deformed to the transverse configuration, the clip 10 may be expanded, e.g., by applying a force radially outwards against an inner surface of the clip 10, thereby expanding the looped elements 30 to the expanded state. The looped elements 30 may then be heat treated, e.g., by heating the clip 10 to an austenitic state, to cause the looped elements 30 to "remember" the expanded state, as is known to those skilled in the art. It may also be necessary to further heat treat the clip 10 further, e.g., with the tines in the planar configuration to cause the body 12 and/or tines 16 to "remember" and be biased towards the planar configuration, as is known to those skilled in the art. The clip 10 may then be cooled, e.g., to a martensitic state, which may be at or close to ambient temperature, and manipulated, e.g., malleably deformed to the transverse configuration, for example, by loading the clip 10 onto a delivery device (not shown), as described below. Thus, if the clip 10 is subsequently heated to a predetermined temperature, e.g., at or below body temperature, the material may remember the planar configuration and/or expanded state and become biased towards them.

Figure 2A:
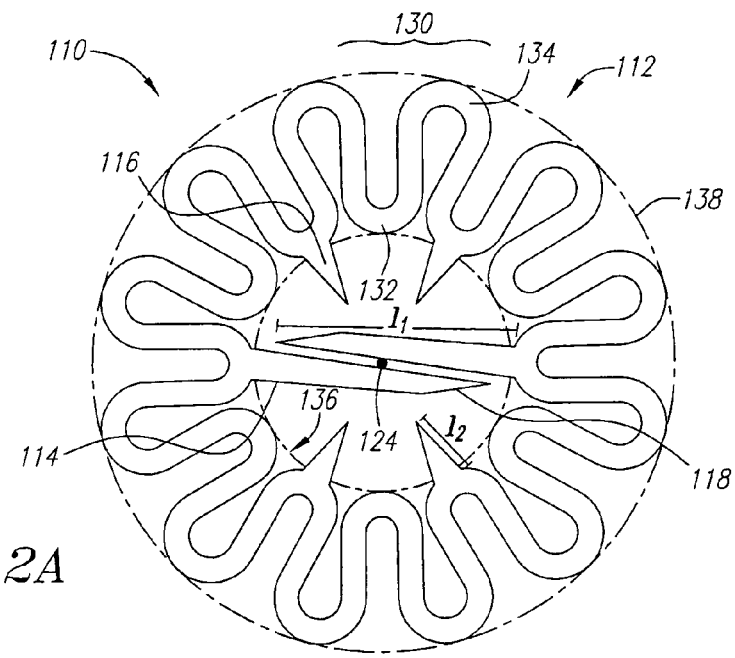
FIG. 2A is a top view of a second embodiment of a clip including a plurality of tines in a planar orientation, in accordance with the present invention.
Figure 2B:
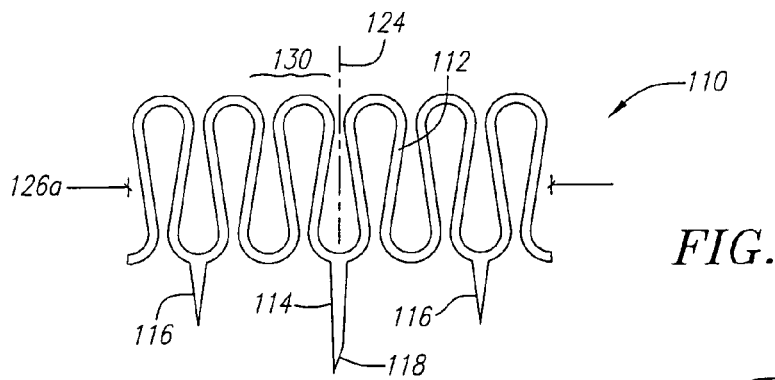
FIGS. 2B and 2C are side views of the clip of FIG. 2A, with the tines oriented substantially transversely from the planar orientation, in compressed and expanded states, respectively.
Figure 2C:
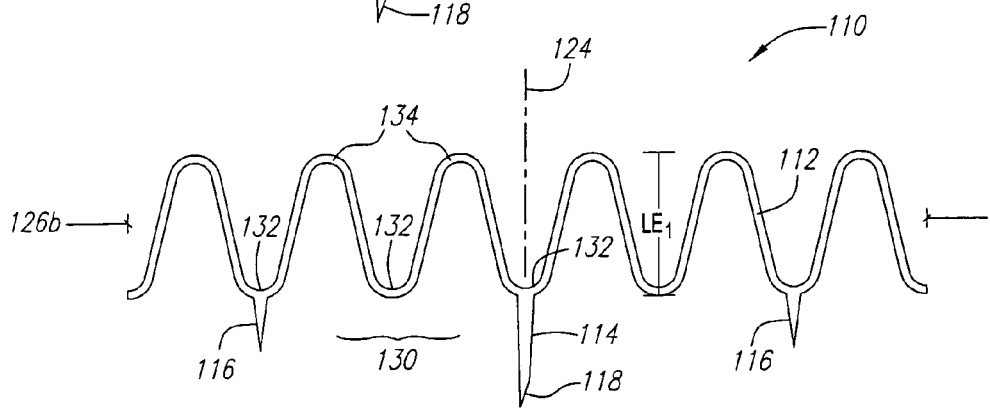

FIGS. 2A–2C show another preferred embodiment of a closure device or clip 110 that includes a generally annular-shaped body 112 defining a plane and disposed about a central axis 124 extending through the plane. The body 112 preferably includes a plurality of looped elements 130 that are connected to one another to form the body 112, similar to the previous embodiment. Each looped element 130 includes an inner or first curved region 132 and an outer or second curved region 134. Similar to the previous embodiment, the first and second curved regions 132, 134 may form an endless sinusoidal pattern or other generally zigzag pattern. When the clip 110 is in a substantially planar configuration, as shown in FIG. 2A, the first curved regions 132 may define an inner periphery 136, and the second curved regions 134 may define an outer periphery.

Unlike the previous embodiment, the clip 110 includes a plurality of primary tines 114 and a plurality of secondary tines 116. Each of the primary and secondary tines 114, 116 may include a variety of known pointed tips, similar to the previous embodiment.

Each of the primary tines 114 may have a length $l_1$, although alternatively each of the primary tines 114 may have a different length than one another. The primary tines 114 may be disposed in one or more opposing pairs, e.g., on opposing first curved regions 132, and may be oriented towards and/or across the central axis 124 in the planar configuration. In the planar configuration, the lengths $l_1$ may be sufficiently long such that the primary tines 114 at least partially overlap one another, i.e., extend across the central axis 124 towards an opposing tine 114. Therefore, the tips of the primary tines 114 may extend past the central axis 124 and/or the primary tines 114 in each pair may lie substantially parallel to each other when the clip 110 is in the planar configuration.

Each of the secondary tines 116 may be disposed on a first or inner curved region 132, e.g., such that one or more secondary tines 116 may be provided between opposing pairs of primary tines 114. Each of the secondary tines 116 may have a length $l_2$ that is substantially less than the length $l_1$ of the primary tines 114.

Preferably, a secondary tine 116 is disposed on either side of each primary tine 114. For example, the clip 110 shown in FIGS. 2A–2C has first and second primary tines 114, and each of the first and second primary tines 114 has a secondary tine 116 on either side of it. Thus, the clip 110 may have a total of two primary tines 114 and four secondary tines 116. Optionally, the secondary tines 116 may be disposed substantially symmetrically about the central axis 124. The tines 114, 116 may be provided on every other first curved regions 132. For example, a first curved region 132 having neither a primary tine 114 nor a secondary tine 116 may separate each adjacent tine, e.g., between two adjacent secondary tines 116, or between a secondary tine 116 and a primary tine 114.

As shown in FIGS. 2B and 2C, the body 112 and/or the tines 114, 116 may be deflected such that they extend transversely with respect to the plane defined in FIG. 2A. Preferably, the primary tines 114 and secondary tines 116 are oriented substantially parallel to the central axis 124 to define a transverse configuration, as shown in FIG. 1B. In the transverse configuration, the body 112 has a generally annular shape defining a length, $LE_1$, that extends generally parallel to the central axis 24, and corresponds generally to an amplitude of the sinusoidal pattern. Preferably, the body 112 is sufficiently flexible such that the clip 110 may assume a generally circular or elliptical shape (not shown), e.g., conforming to an exterior surface of a delivery device (not shown).

The tines 114, 116 may be biased towards one another and/or towards the central axis 124, i.e., due to the bias of the clip 110 towards the planar configuration of FIG. 2A, similar to the previous embodiment. With the clip 110 in the transverse configuration, the clip 110 may be delivered such that the primary tines 114 entirely penetrate the wall of a blood vessel or other body lumen, while the secondary tines 116 only partially penetrate the wall due to their relative lengths, as explained further below.

The looped elements 130 may be expandable between a compressed state, as shown in FIG. 2B, and an expanded state, as shown in FIG. 2C, similar to the previous embodiment. Preferably, the looped elements 130 are biased to the expanded state, but may be resiliently compressed to the compressed state, e.g., by constraining the clip 110.

Figure 3:
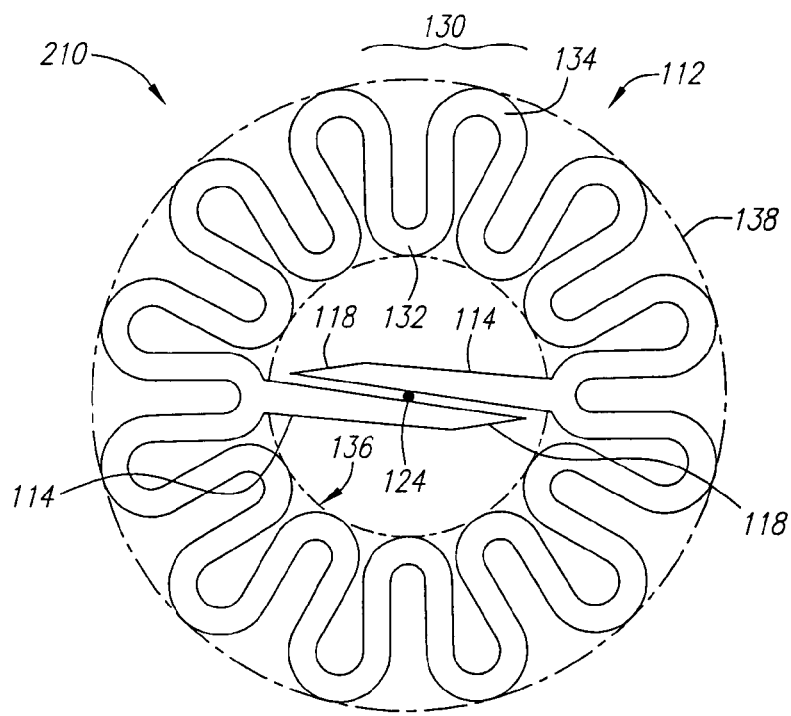
FIG. 3 is a top view of a third embodiment of a clip, in accordance with the present invention.

Turning to FIG. 3, an alternative embodiment of a clip 210 is shown that includes a body 112 including looped elements 130, and primary tines 114, similar to the previous embodiment, but has no supplemental or secondary tines 116. The reference numbers for elements of the clip 210 are consistent with like elements used for the clip 110.

Any of the clips of the present invention may include one or more radiopaque markers or other markers visible using external imaging, such as fluoroscopy. For example, using the clip 110 of FIGS. 2A–2C as an example, the entire clip 110 may be coated with radiopaque material, which may be a high density material such as gold, platinum, platinum/iridium, and the like.

Alternatively, the clip 110 may be partially coated with radiopaque material by using masking techniques. For example, the entire clip 110 may first be coated with radiopaque material. The clip 110 may then be masked at locations where the radiopaque coating is desired. For example, the looped elements 130 of the clip 110 may be left unmasked during this process if it is desired to leave the looped elements 130 uncoated by radiopaque material. This may be desirable, e.g., to prevent radiopaque material from adversely affecting the flexibility of the looped elements 130. The clip 110 may then be treated to remove the radiopaque material from the unmasked areas, in this example, the looped elements 130. The masking may then be removed using conventional processes, leaving the rest of the clip 110 coated with radiopaque material.

Figure 4:
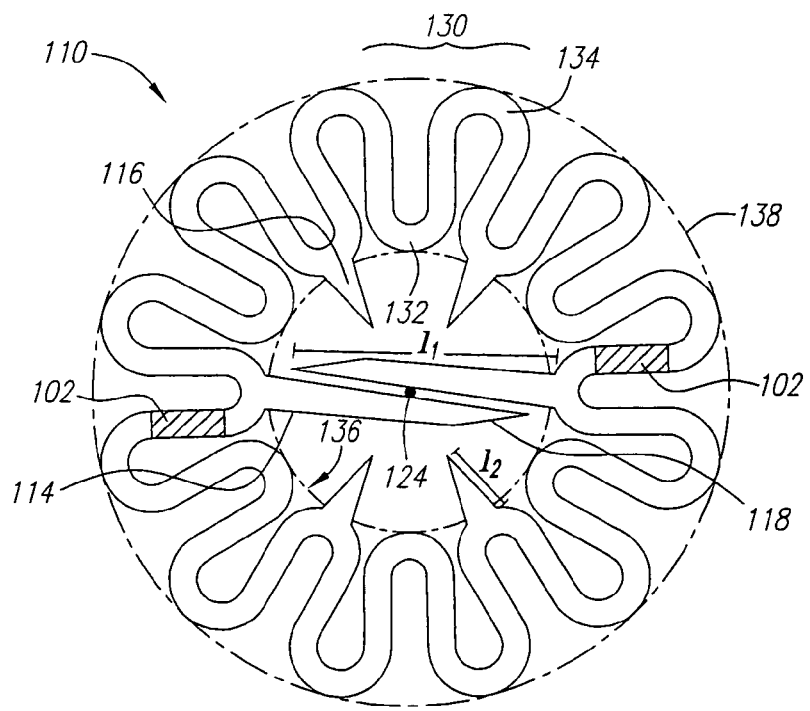
FIG. 4 is a top view of an embodiment of a clip having radiopaque markers thereon.
Figure 5:
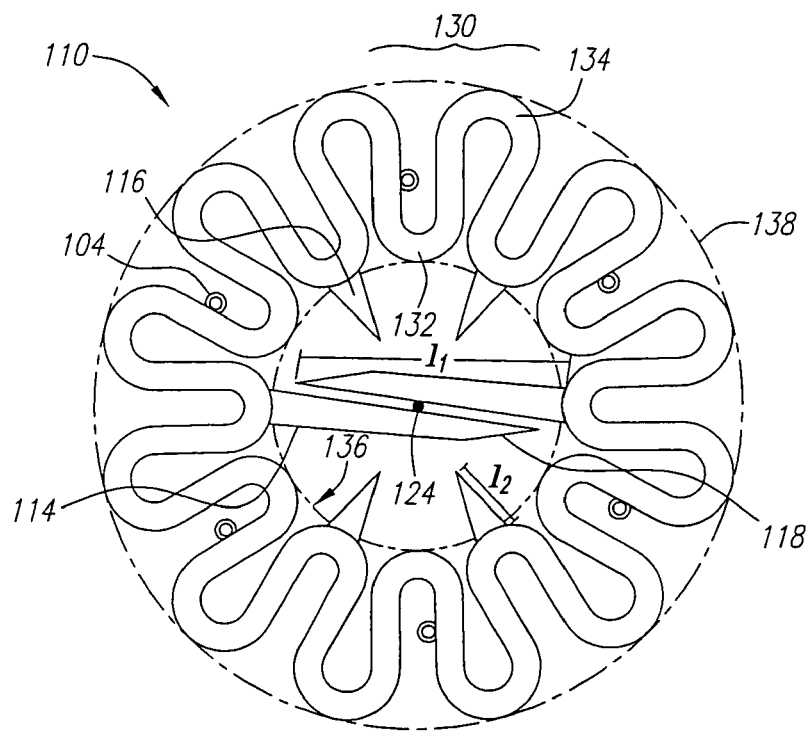
FIG. 5 is a top view of an embodiment of a clip having pockets for holding radiopaque markers therein.

Turning to FIG. 4, in another alternative, one or more discrete markers 102 may be provided at predetermined locations on the clip 110. For example, high density or radiopaque material 102 may be crimped or otherwise secured onto opposing double looped or circular regions 130. In another embodiment, shown in FIG. 5, a plurality of pockets 104 may be provided on the looped elements 130 into which high density plugs (not shown) may be bonded or otherwise secured. These various radiopaque markers may also be incorporated in any of the embodiments described herein.

Figure 6:
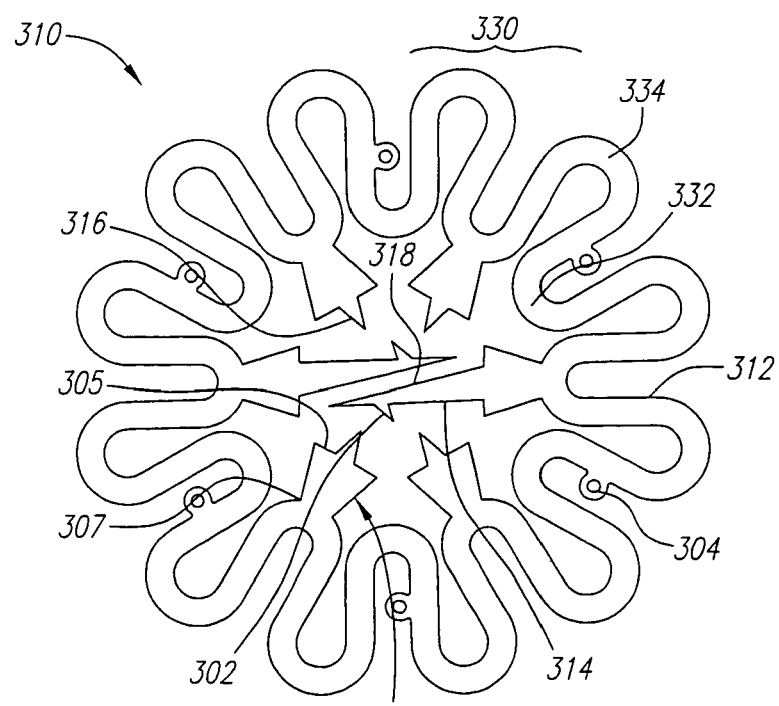
FIG. 6 is a top view of another embodiment of a clip including stop elements, in accordance with the present invention.

Turning to FIG. 6, another embodiment of a clip 310 is shown that, similar to clip 110, may include a plurality of looped elements 330 that interconnect to form a body 312. Each looped element 330 may have a first or inner curved region 332 and a second or outer curved region 334. Primary tines 314 may be disposed on opposing first curved regions 332, which, optionally, may include a barb 302 thereon to enhance engagement with tissue. Secondary tines 316 may be provided on first curved regions 332 on either side of each primary tine 314. In addition, a first curved region 332 without a tine 314, 316 may separate adjacent tines, as described above with regard to the previous embodiments.

The clip 310 also includes stop members 306 on one or more of the tines 314, 316, e.g., adjacent the respective first curved region 332. Each stop member 306 may be blunt-shaped, e.g., generally triangularly with an apex 307 of the stop member 306 extending from the first curved region 332, and the tine 314, 316 extending from a wide or blunt base 307 of the stop member 306. During use, the blunt bases 307 may limit penetration of the respective tines 314, 316 into tissue by reducing an effective length of the respective tine 314, 316. For example, when the tines 314, 316 are driven into tissue, the tines 314, 316 may penetrate the tissue until the blunt bases 307 contact the tissue, whereupon the tines 314, 316 may be prevented from penetrating further into the tissue.

Figure 7:
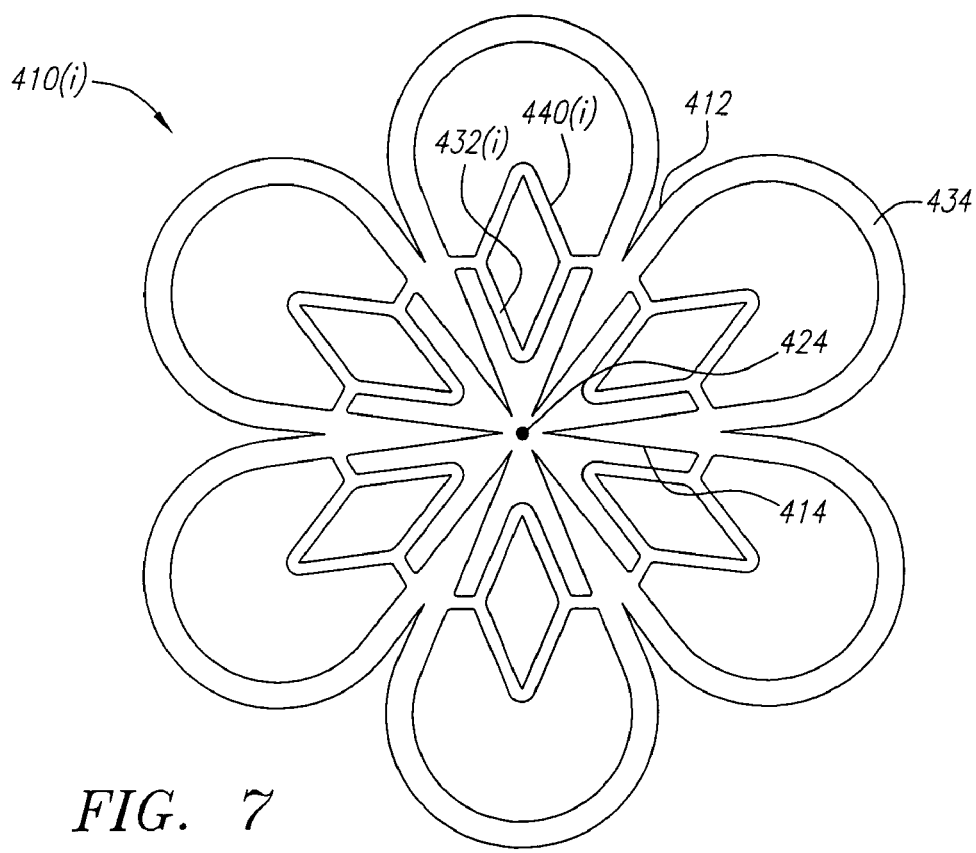
FIG. 7 is a top view of yet another embodiment of a clip including stop elements, in accordance with the present invention.

Turning to FIG. 7, another embodiment of a clip 410(i) is shown that includes a body 412, a plurality of tines 414, and a plurality of spring elements 440(i) that interconnect between adjacent tines 414. The body 412 includes outer curved regions 434 that extend between adjacent tines 414, thereby defining an outer periphery for the clip 410(i). The clip 410(i) may be moveable between a substantially planar configuration such as that shown in FIG. 7, and a transverse configuration (not shown), and preferably is biased towards the planar configuration, similar to the previous embodiments.

In the embodiment shown, the spring elements 440(i) generally are hollow diamond shaped elements, including curved inner regions 432(i) oriented towards the central axis 424 of the body 412 when the clip 410(i) is in the planar configuration. The spring elements 440(i) may serve multiple purposes. First, the spring elements 440(i) may bias the clip 410(i), e.g., allowing the clip 410(i) to at least partially expand resiliently. For example, when the clip 410(i) is deflected into the transverse configuration (not shown), the spring elements 440(i) may allow the tines 414 to be moved away from the central axis 424 and/or one another. Thus, during deployment, the tines 414 may be deflected radially outwardly or otherwise expanded to engage a larger area of tissue.

As the tines 414 are expanded, the spring elements 414(i) may deform to become wider (along a dimension extending generally between the adjacent tines 414) and shorter (along a dimension extending generally parallel to the tines 414). Once a force causing the tines 414 to expand is removed, the spring elements 414(i) may resiliently try to return towards their original shape, thereby pulling the tines 414 closer towards one another.

In addition, the curved inner regions 432(*i*) of the spring elements 414(*i*) may provide stops limiting penetration of the tines 414 into tissue, similar to the stop members described above. For example, when the clip 410(*i*) is in the transverse configuration and the spring elements 414(*i*) are expanded, the curved inner regions 432(*i*) may be become more oblique, possibly becoming generally linear. Thus, when the tines 414 are driven into tissue, the curved inner regions 432(*i*) may limit penetration of the tines 414.

Finally, after the clip 410(*i*) is deployed, e.g., the tines 414 are penetrated into tissue, the curved inner regions 432(*i*) may return towards their original shape, and may pinch or otherwise engage tissue between the inner curved regions 432(*i*) and the adjacent tines 414. Thus, contracting the spring elements 440(*i*) may enhance the ability of the clip 410(*i*) to seal a puncture site, e.g., by pulling engaged tissue inwardly towards the central axis 424 of the clip 410(*i*).

Figure 8:
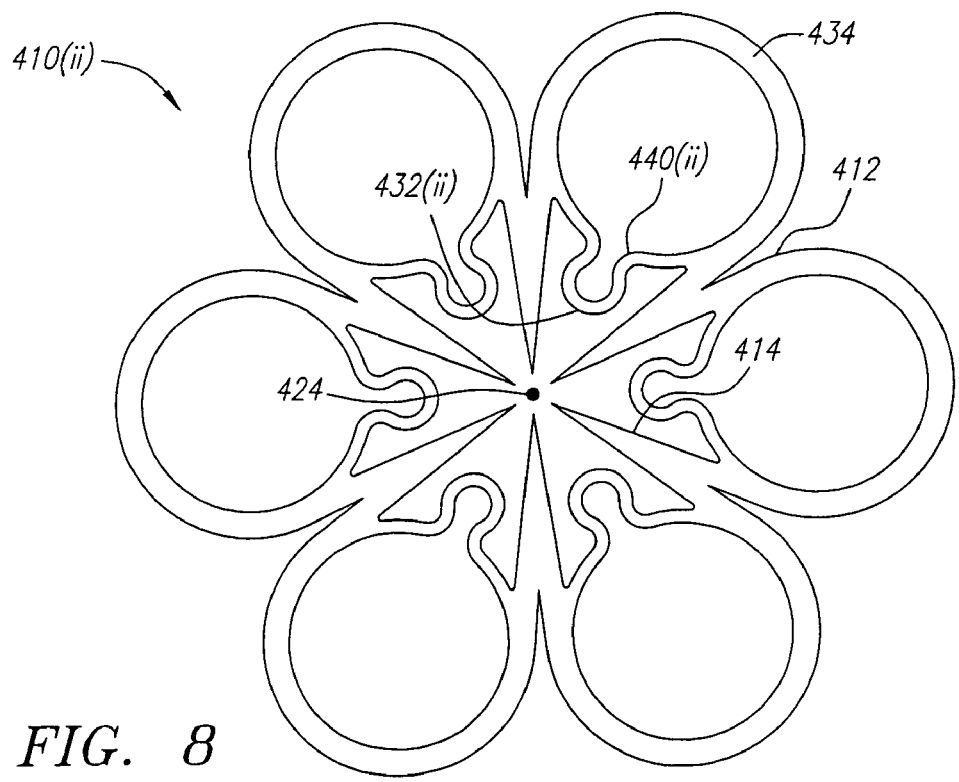
FIG. 8 is a top view of still another embodiment of a clip including stop elements, in accordance with the present invention.

Turning to FIG. 8, an alternative embodiment of a clip 410(*ii*) is shown that is substantially similar to the clip 410(*i*) shown in FIG. 7, with the exception of the shape of the spring elements 440(*ii*). Rather than diamond shaped elements, the spring elements 440(*ii*) are looped elements generally defining a circular shape.

Figure 12:
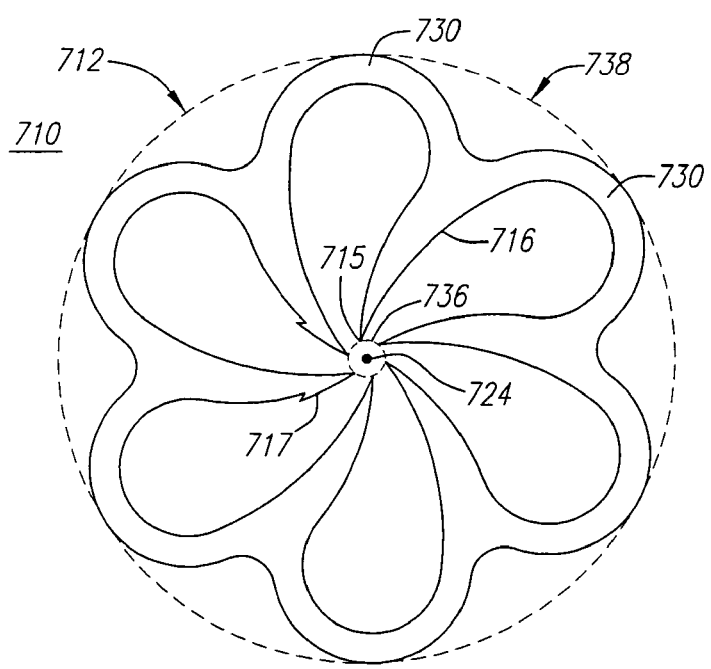
FIG. 12 is a top view of an embodiment of a clip having arcuate tines, in accordance with the present invention.

Turning now to FIG. 12, another preferred embodiment of a clip 710 of the present invention is illustrated. Similar to the previous embodiments, the clip 710 includes a generally annular-shaped body 712 that defines a plane. The body 712 is disposed about a central axis 724 that extends through the plane. The body 712 preferably includes a plurality of outer curved elements 730 that extend between adjacent tines 716 and are connected to each other to form the body 712. When the clip 710 is in a substantially planar configuration, as shown in FIG. 12, the curved elements 730 define an outer periphery 738 of the clip 710.

The tines 716 are curved or arcuately shaped and include distal tips 715 that extend toward the central axis 724 when the clip 710 is in the substantially planar configuration. Optionally, one or more of the tines 716 may include barbs 717, similar to the previous embodiments. Preferably, the curve of the tines 716 are all in phase with one another such that the tines 716 spiral about the central axis 724. This may allow a length of the tines 716 to be maximized for a given diameter of the body 712.

For example, the tines 716 may have a length that is greater than a radius of the body 712 without the distal tips 715 of the tines 716 touching one another. Thus, due to the arcuate shape of each tine 716, the tines 716 of clip 710 may be generally longer than the straight tines of the previous clips having comparable diameters. The tines 716 may, therefore, penetrate deeper into tissue than the tines of the other clips.

As with the previous embodiments, the body 712 and/or the tines 716 of clip 710 may be deflected until the tines 716 extend transversely with respect to the plane defined in the planar configuration, thereby defining a transverse configuration. In the transverse configuration, the tines 716 may be oriented substantially parallel to the central axis 724. Additionally, as with the previous embodiments, the tines 716 and/or body 712 may be biased to move from the transverse configuration towards the planar configuration. The clip 710 may be delivered in substantially the same manner as will be described with respect to other clips of the present invention.

Any of the clips of the present invention may be coated with a substance that enhances hemostasis and/or healing of a blood vessel, e.g., by increasing a rate of regeneration of endothelium on the interior surface of the vessel, or by decreasing inflammatory response at the treatment site. In one embodiment, a suitable synthetic peptide coating may be applied to a clip to attract endothelial cells to the surface. An exemplary synthetic peptide coating may, for example, attach to the same cell binding sites as collagen. In another embodiment, a clip may be coated with a combination of clotting factors in order to promote hemostasis. For example, one side of the clip may be coated with Factor III and an endopeptidase, such as PTA, to accelerate the intrinsic clotting pathway. On the opposite side of the clip, a combination of a protein cofactor proaccelerin (Factor V) and an activated endopeptidase, such as serum prothrombin conversion accelerator (SPCA), cothromboplastin, and the like, may be applied to accelerate the extrinsic clotting pathway. The clips of the present invention may also be coated with any suitable hydrophilic polymer that swells in the presence of bodily fluids in order to reduce, minimize, or stop blood flow, thereby aiding the hemostasis process.

Figure 9:
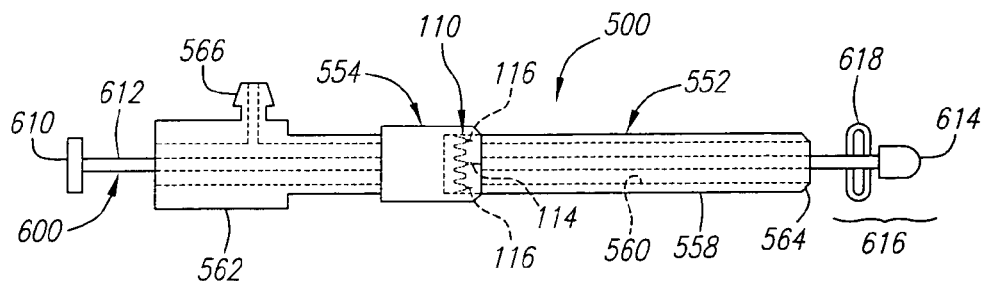
FIG. 9 is a side view of an apparatus, including an introducer sheath and an obturator, suitable for delivering a clip of the present invention.

The clips of the present invention may be delivered using various apparatus and methods. An exemplary apparatus 500 suitable for delivering a clip of the present invention is shown in FIG. 9. Other suitable apparatus that may be used to deliver a clip of the present invention are disclosed in co-pending U.S. application Ser. No. 10/0821,723, filed on the same day as the present application and entitled "Apparatus and Methods for Delivering a Closure Device", which is assigned to the assignee of the present application. The disclosures of this application and any references cited therein are expressly incorporated by reference.

Generally, the apparatus 500 includes an introducer sheath 552, and a housing or carrier assembly 554 slidably disposed on the sheath 552. The sheath 552 includes a substantially flexible or semi-rigid tubular body 558 including a lumen 560 extending between its proximal and distal ends 562, 564. The distal end 564 has a size and shape configured to facilitate insertion into a blood vessel, e.g., having a tapered tip for facilitating substantially atraumatic introduction through the passage and at least partially into the vessel. The lumen 560 has a size for inserting one or more devices therethrough, such as a catheter, guidewire, and the like (not shown). The sheath 552 also preferably includes one or more seals (not shown), such as a hemostatic valve, within the lumen 560 at or near the proximal end 562 that provides a fluid-tight seal, yet accommodates inserting one or more devices into the lumen 560 without fluid passing proximally from the sheath 552.

Optionally, the sheath 552 may include a side port 566 that communicates with the lumen 560, for example, to deliver fluids into the lumen 560. Alternatively, or in addition, the side port 566 may be used to provide a "bleed back" indicator. An exemplary "bleed back" indicator and related methods of use are disclosed in co-pending application Ser. No. 09/680,837, filed Oct. 6, 2000, entitled "Apparatus and Methods for Positioning a Vascular Sheath," which is assigned to the assignee of the present application. The disclosure of this application and any other references cited therein are fully incorporated by reference herein.

The apparatus 500 may also include a mechanical locator or obturator 600, such as that disclosed in U.S. application Ser. No. 10/081,723, incorporated by referenced above, that may be part of an actuator assembly (not shown) that is attachable to the proximal end of the sheath 552. Alternatively, the mechanical locator or obturator 600 may be a separate device that is insertable into the lumen 560, e.g., through the actuator assembly. Generally, the obturator 600 is an elongate member including a distal tip 614 and a distal portion 616. The distal tip 614 may be substantially soft and/or flexible such that the distal tip 614 may substantially atraumatically enter the vessel 590 (not shown, see FIGS. 10A–10D). The distal portion 616 generally includes one or more wings or other expandable elements 618 for providing tactile feedback, as described further below.

The carrier assembly 554 is slidably disposed on an exterior of the sheath 552, and is configured for releasably carrying a clip 110 (shown in phantom), which may any of the clips described herein. The carrier assembly 554 may be substantially permanently attached to the sheath 552 and/or may be actuated from the proximal end 562 of the sheath 552, for example, by the actuator assembly (not shown), to advance the clip 110 distally during deployment. Alternatively, the clip 110 may be carried by an actuator assembly, as disclosed in co-pending U.S. application Ser. No. 10/081, 725, filed on the same day as the present application and entitled "Sheath Apparatus and Methods for Delivering a Closure Device," which is assigned to the assignee of the present application. The disclosures of this application and any references cited therein are expressly incorporated herein by reference.

Turning to FIGS. 10A–D, the apparatus 500 may be used to deliver the clip 110 to close and/or seal an incision, puncture, or other passage 592 that extends from a patient's skin 594, through intervening tissue 596, and into a wall 598 of a vessel 590 or other body lumen. Alternatively, the apparatus 500 may be used to deliver the clip 110 to engage tissue in other procedures, e.g., to connect tissue segments together or otherwise to secure tissue structures with respect to one another. For example, the apparatus 500 and clip 110 may be used to attach an anastomosis during a bypass procedure. It will be appreciated by those skilled in the art that the clip 110 and/or apparatus 500 may be useful in a variety of procedures.

Figure 10A:
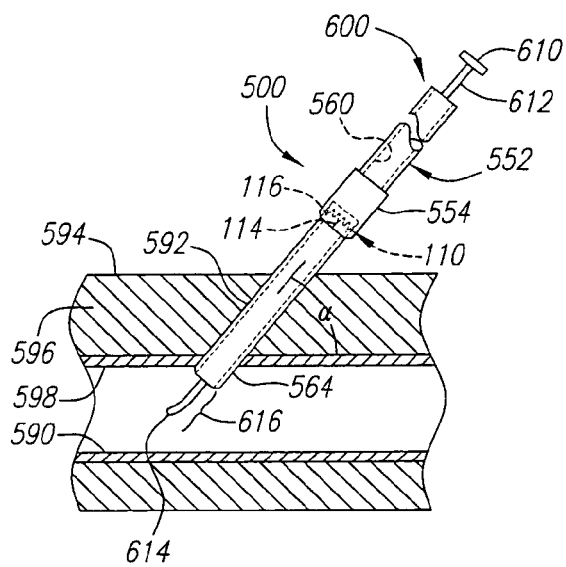
FIGS. 10A–10D are cross-sectional views of a blood vessel, showing a method for delivering a clip into a passage communicating with the vessel using the apparatus of FIG. 9.

As shown in FIG. 10A, the sheath 552 may be inserted or otherwise positioned within the vessel 590, i.e., through the passage 592. The sheath 552 may be advanced over a guidewire or other rail (not shown) previously positioned through the passage 592 into the vessel 590 or advanced in conjunction with a pointed stylet directly through tissue using conventional procedures. Preferably, the vessel 590 is a peripheral vessel, such as a femoral, radial, or carotid artery, although other body lumens may be accessed using the sheath 552, as will be appreciated by those skilled in the art.

The passage 592, and consequently the sheath 552, may be oriented at an angle "alpha" with respect to the vessel 590, thereby facilitating introducing devices through the lumen 560 of the sheath 552 into the vessel 590 with minimal risk of damage to the vessel 590. One or more devices, such as a guide wire, a catheter, and the like (not shown), may be inserted through the sheath 552 and advanced to a desired location within the patient's body. For example, the devices may be used to perform a therapeutic or diagnostic procedure, such as angioplasty, atherectomy, stent implantation, and the like, within the patient's vasculature.

After the procedure is complete, any devices used during the procedure may be removed from the sheath 552, and the obturator 600 may be inserted into the lumen 560. For example, the obturator 600 may be part of an actuator assembly (not shown), and may be advanced through the lumen when the actuator assembly is attached to the proximal end of the sheath 552. Alternatively, the actuator assembly and obturator 600 may be coupled separately to the sheath 552.

When the obturator 600 is fully inserted within the sheath 552, the distal portion 616 of the obturator 600 may extend beyond the distal end 564 of the sheath 552. In an alternative embodiment, the obturator 600 may be attached to an exterior surface (not shown) of the sheath 552, for example, along a track, e.g., including cooperating slots, grooves, and the like (not shown) in the sheath 552 and obturator 600.

Figure 10B:
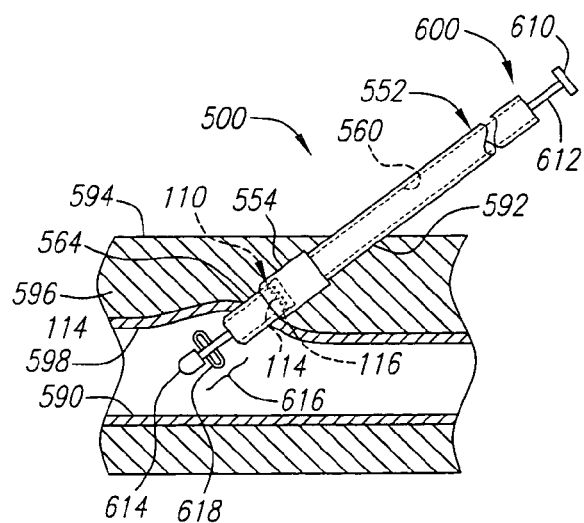

Turning to FIG. 10B, the expandable elements 618 on the distal portion of the obturator 600 may then be directed to their expanded configuration, for example, by activating a switch on the proximal end (not shown) of the obturator 600. With the sheath 552 and obturator 600 coupled to one another, the sheath 552 and obturator 600 may be moved in conjunction with one another.

Figure 10C:
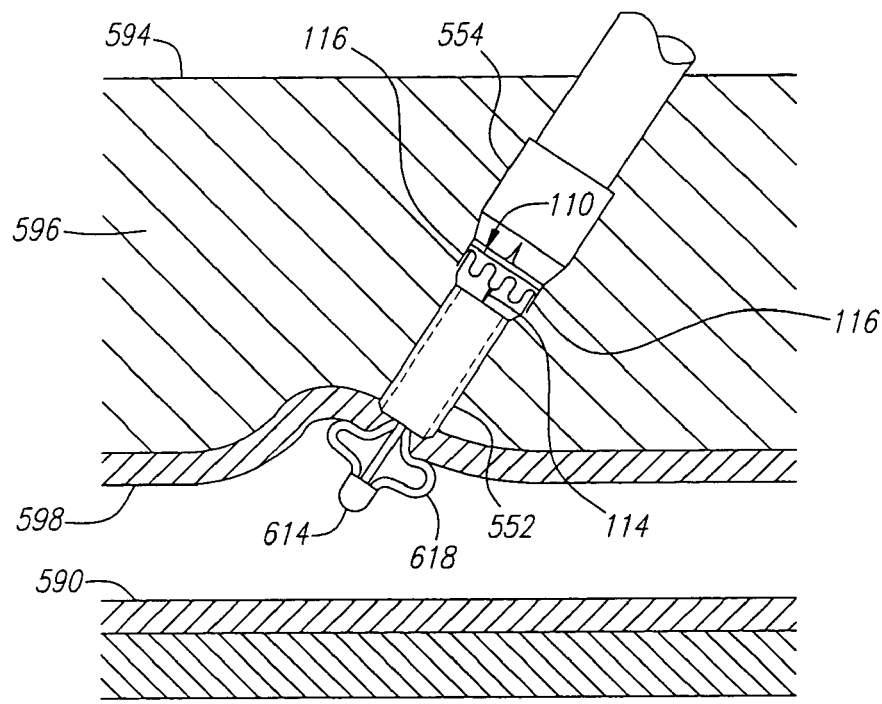

As shown in FIG. 10C, the sheath 552 may be partially withdrawn from the vessel 590, until the expandable elements 618 contact the wall 598 of the vessel 590. Thus, the expandable elements 618 may provide a tactile indication of the position of the sheath 552 with respect to the wall 598 of the vessel 590. In addition, the expandable elements 618 may assist in "presenting" the wall 598 of the vessel 590, e.g., for receiving the clip 110.

Generally, the clip 110 is carried by the carrier assembly 554 before the procedure. The clip 110 may be constrained in its transverse configuration on the carrier assembly 554, and the carrier assembly 554 may be provided on or adjacent the proximal end of the sheath 552. Because the tines, which may include primary and secondary tines 114, 116 may be biased towards one another, the tines 114, 116 may slidably contact an inner surface (not shown) of the carrier assembly 554 or an outer surface of the sheath 552, thereby constraining the clip 110 in its transverse configuration.

Figure 10D:
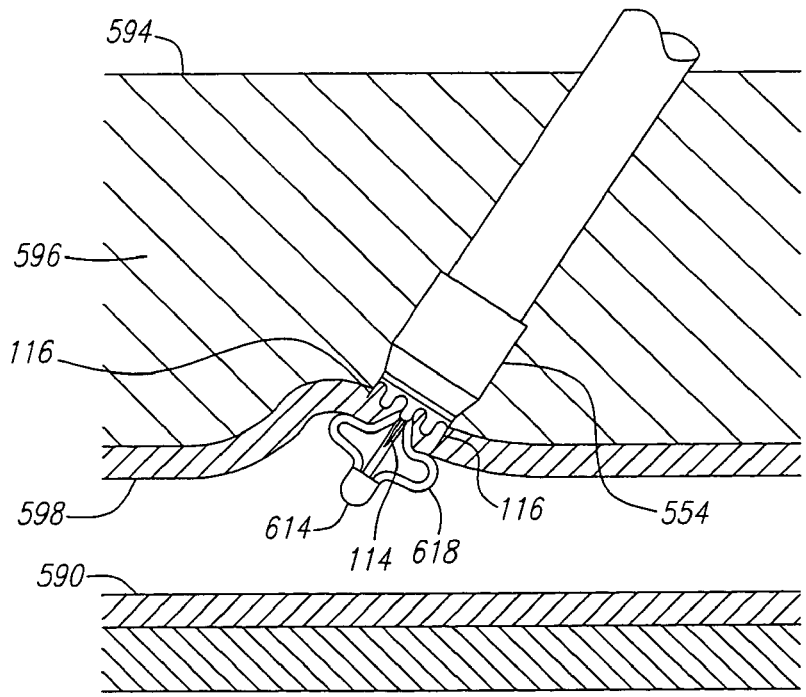

Turning to FIG. 10D, with the sheath 552 properly positioned, the carrier assembly 554 may then be actuated, for example, to advance the carrier assembly 554 distally over the sheath 552 to deliver the clip 110. Preferably, the carrier assembly 554 may only be advanced a predetermined fixed distance relative to the distal end of the sheath 552, and consequently, the expandable elements 618 of the obturator 600, such that the clip 110 substantially engages the wall 598 of the blood vessel 590. This predetermined distance may facilitate properly deploying the clip 110 with respect to the wall 598 of the vessel 590, e.g., to prevent advancing the clip 110 too far, i.e., into the vessel 590.

As the clip 110 is deployed from the carrier assembly 554, the clip 110 may be expanded to an enlarged diameter. For example, a distal end of the carrier assembly 554 may include a ramped region (not shown) that may deflect the tines 114, 116, and/or the body of the clip 110 radially outwardly. As the clip 110 is advanced over the ramped region, the tines 114, 116 may be deflected radially outwardly as they are being driven into the surrounding tissue, thereby engaging a larger region of tissue than if the tines 114, 116 had been maintained substantially axially.

Alternatively, the clip 110 may include expandable looped elements and/or spring elements (not shown), such as those described above, that may facilitate expanding the clip 110 as it is deployed from the carrier assembly 554 and/or the sheath 552. For example, the looped elements of the clip 110 may be compressed when the clip 110 is loaded into the carrier assembly 554, e.g., thereby allowing a relatively smaller profile carrier assembly 554 to be used. The clip 110 may automatically expand upon deployment from the carrier assembly 554 to engage a larger region of tissue surrounding the opening, such as an arteriotomy 591 in the wall 598 of the vessel 590 (see FIG. 11A).

Figure 11A:
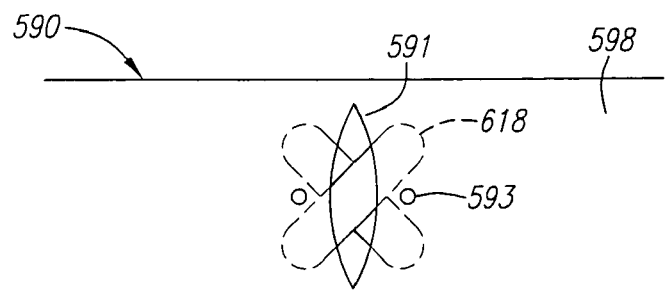
FIG. 11A is a top view of the blood vessel of FIGS. 10A–10D, showing the orientation of the expandable elements of the obturator and openings produced by primary tines of the clip relative to an arteriotomy in the vessel.
Figure 11B:
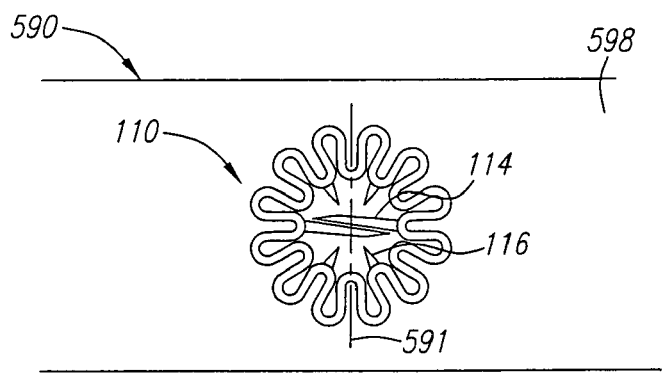
FIG. 11B is a top view of the blood vessel of FIG. 11A, showing the arteriotomy being closed by the clip.

Once the clip 110 is deployed entirely or otherwise released from the sheath 552, the clip 110 may resiliently move towards its substantially planar configuration, such as that shown in FIG. 11B.

During delivery of the clip 110, radiopaque markers (not shown) on the clip 110, the carrier assembly 554, and/or the expandable members 618 may be monitored, e.g., using fluoroscopy, to facilitate observing and/or positioning the apparatus 500. Thus, a relative position of the clip 110 with respect to the expandable elements 618, and consequently to the wall 598 of the vessel 590, may be ascertained before the clip 110 is deployed from the carrier assembly 554.

Turning to FIGS. 11A and 11B, in a preferred embodiment, the expandable elements 618 of the obturator 600 may be rotationally offset from the one or more tines 114 on the clip 110. For example, if the clip 110 includes primary tines (such as those shown in FIGS. 2A and 3), the obturator 600 and clip 110 may have a predetermined relative angular orientation about the central axis 124. Preferably, the clip 110 is loaded onto the carrier assembly 554 in a predetermined angular orientation and the obturator 600 is receivable in the sheath 552 only in a predetermined angular orientation that is offset such that the tines 114, 116 are out of axial alignment with the expandable elements 618, as shown in FIG. 11A.

This predetermined rotational orientation may substantially minimize the possibility of the primary tines 114 contacting and/or damaging the expandable elements 618. For example, with particular reference to FIG. 11A, a preferred relative angular orientation of the clip 100 and obturator 600 is shown relative to an arteriotomy 591 in the wall 598 of the vessel 590. Here, the expandable elements 618 are oriented to crisscross diagonally the arteriotomy 591 within the interior of the vessel 590. Generally, because of the natural structure of the tissue in the wall of a vessel, an arteriotomy generally tends to adopt an elongate shape that extends transversely to the direction of flow (i.e., across the circumference of the vessel wall).

The primary tines 114 are oriented such that the primary tines 114 pierce the wall 598 of the vessel 590 on either side of the arteriotomy 591, as shown. With the expandable elements 618 crisscrossing diagonally, risk of contact with the primary tines 114 is substantially reduced. Thus, the primary tines 114 may be sufficiently long to extend entirely through the wall 598 of the vessel 590 while avoiding the expandable elements 618.

The expandable elements 618 may then be collapsed and/or withdrawn into the distal end 564 of the sheath 552. As the clip 110 is released entirely from the sheath 552, the primary tines 114 may partially overlap, as shown in FIG. 11B, thereby pulling the arteriotomy 591 closed, similar to a single-thread suture. For example, the expandable elements 618 may be automatically collapsed immediately before or after the clip 110 is deployed from the carrier assembly 554 or when the carrier assembly 554 reaches its extreme distal position. Preferably, the distal portion 616 of the obturator 600 is collapsed and retracted into the sheath 554 after the primary tines 114 have pierced the wall 598 of the vessel 590, but before the clip 110 is entirely released from the sheath 552.

In addition, if the clip 110 includes secondary tines 116 (such as those shown in FIG. 2A), the secondary tines 116 may partially penetrate the wall 598 of the vessel 590 during deployment of the clip 110. Preferably, the lengths of the secondary tines 116 are relatively short or stop members (not shown) may be provided that prevent the secondary tines 116 from piercing entirely through the wall 598. When the clip 110 is released, the secondary tines 116 may pull the tissue inwardly, behaving somewhat similarly to a purse-string suture, to enhance closing the arteriotomy 591.

Once the clip 110 is successfully deployed into the wall 598 of the vessel 590, e.g., on either side of an arteriotomy 591, the apparatus 500 may be withdrawn from the passage 592. The entire apparatus 500 may be removed in one step, or alternatively, the obturator 600 may first be withdrawn from the sheath 552 before withdrawing the sheath 552, thereby leaving the clip 110 in place to close the arteriotomy 591 and/or seal the passage 592. In addition, if desired, a sealant or other material may be introduced into the passage 592 in conjunction with or separate from delivery of the clip 110 to further seal the passage 592, as is known to those skilled in the art.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for closing an opening in a wall of a body lumen, comprising:
   advancing a distal end of an elongate member through a passage and into a body lumen;
   positioning an obturator distally beyond the distal end of the elongate member along the passage within the body lumen;
   expanding one or more expandable elements of the obturator;
   withdrawing the obturator from the passage until an expandable element contacts an inner wall of the body lumen, thereby providing a tactile indication of the inner wall of the body lumen;
   advancing a clip having tines into the passage over the elongate member until the tines of the clip engage the wall of the body lumen; and
   withdrawing the elongate member from the body lumen and passage, leaving the clip to substantially close the opening in the wall of the body lumen, and a plurality of the tines and the clip translating into a substantially planar configuration.

2. The method of claim 1, further comprising providing a carrier assembly on the elongate member, the carrier assembly carrying the clip.

3. The method of claim 1, wherein the tines comprise primary tines and secondary tines, and wherein advancing the clip comprises:
   puncturing the wall of the body lumen with the primary tines until tips of the primary tines enter the body lumen; and
   engaging the wall of the body lumen with the secondary tines.

4. The method of claim 3, wherein the secondary tines further include tissue stops.

5. The method of claim 2, wherein the passage is defined by a sheath.

6. The method of claim 1, wherein the clip is constructed of a superelastic material.

7. The method of claim 6, wherein the clip is nitinol.

8. The method of claim 1, wherein the expandable elements of the obturator retract simultaneously with the advancing of the clip.

9. The method of claim 1, further comprising the step of expanding the clip prior to advancing.

* * * * *

UNITED STATES PATENT AND TRADEMARK OFFICE
CERTIFICATE OF CORRECTION

PATENT NO.         : 7,001,398 B2
APPLICATION NO. : 10/617090
DATED                  : February 21, 2006
INVENTOR(S)       : Michael T. Carley et al.

It is certified that error appears in the above-identified patent and that said Letters Patent is hereby corrected as shown below:

Column 2
Lines 59 and 60, change "facilitating" to --facilitate--

Column 9
Line 15, change "24" to --124--

Column 10
Line 23, change "triangularly" to --triangular--
Line 26, before "of the stop" change "307" to --305--
Line 26, after "blunt bases" change "307" to --305--
Line 31, change "307" to --305--
Line 42, after "configuration" insert --,--
Line 60, change "414(i)" to --440(i)--
Line 65, change "414(i)" to --440(i)--

Column 11
Line 2, change "414(i)" to --440(i)--
Line 5, change "414(i)" to --440(i)--

Column 12
Line 23, change "10/0821,723," to --10/081,723,--

Column 15
Line 32, change "100" to --110--

UNITED STATES PATENT AND TRADEMARK OFFICE
CERTIFICATE OF CORRECTION

PATENT NO. : 7,001,398 B2
APPLICATION NO. : 10/617090
DATED : February 21, 2006
INVENTOR(S) : Michael T. Carley et al.

It is certified that error appears in the above-identified patent and that said Letters Patent is hereby corrected as shown below:

Column 16
Line 1, after "short" insert --,--
Line 64, change "claim 2" to --claim 1--

Signed and Sealed this

Nineteenth Day of September, 2006

JON W. DUDAS
*Director of the United States Patent and Trademark Office*